United States Patent [19]

Convent

[11] 4,045,210

[45] Aug. 30, 1977

[54] SYNERGISTIC HERBICIDAL COMPOSITION COMPRISING N-(BUTOXYMETHYL)-6'-TERT-BUTYL-2-CHLORO-o-ACETOTOLUIDIDE AND N-(3-CHLORO-4-METHYL PHENYL)-N',N'-DIMETHYLUREA

[75] Inventor: Bernard Convent, Leernes, Belgium

[73] Assignee: Monsanto Company, St. Louis, Mo.

[21] Appl. No.: 605,566

[22] Filed: Aug. 18, 1975

[51] Int. Cl.$^2$ .................. A01N 9/20; A01N 9/02
[52] U.S. Cl. .................................. 71/120; 71/76; 71/118
[58] Field of Search .................. 71/118, 120

[56] References Cited

U.S. PATENT DOCUMENTS

| | | | |
|---|---|---|---|
| 3,442,945 | 5/1969 | Olin | 71/118 |
| 3,547,620 | 12/1970 | Olin | 71/118 |
| 3,897,242 | 7/1975 | Martin | 71/120 |
| 3,912,489 | 10/1975 | Fischer | 71/120 |
| 3,955,959 | 5/1976 | Skipper | 71/118 |

*Primary Examiner*—Glennon H. Hollrah
*Attorney, Agent, or Firm*—William I. Andress; Donald W. Peterson

[57] ABSTRACT

A synergistic herbicidal composition comprising as the active ingredient a mixture of N-(butoxymethyl)-6'-tert-butyl-2-chloro-o-acetotoluidide and N-(3-chloro-4-methyl phenyl)-N',N'-dimethylurea (common name chlortoluron) and use of said composition particularly in cereal crops.

8 Claims, No Drawings

SYNERGISTIC HERBICIDAL COMPOSITION COMPRISING N-(BUTOXYMETHYL)-6'-TERT-BUTYL-2-CHLORO-o-ACETOTOLUIDIDE AND N-(3-CHLORO-4-METHYL PHENYL)-N',N'-DIMETHYLUREA

BACKGROUND OF THE INVENTION

1. Field of the Invention

The invention herein pertains to the field of herbicides. In particular, the invention pertains to a synergistic herbicidal composition having as the active ingredient a mixture of N-(butoxymethyl)-6'-tert-butyl-2-chloro-o-acetotoluidide and N-(3-chloro-4-methyl phenyl)-N',N'-dimethylurea (chlortoluron). The herbicidal composition herein has particular application in the control of undesired plants associated with cereal crops, e.g., wheat and barley.

2. Description of the Prior Art

It is known in the prior art to use various N-halo-substituted- and/or alkyl-substituted phenyl-N',N'-dialiphatic ureas (sometimes referred to as "trisubstituted ureas") as herbicides, either individually or in combination with various other herbicidal compounds. In such urea compounds, the aliphatic substituents are commonly alkyl, alkenyl, alkoxy groups, but other groups may also be used.

A wide variety of chemical compounds have been admixed with various members of the above-mentioned class of trisubstituted ureas in efforts to discover new herbicidal compositions having unique additive, antagonistic or synergistic properties with respect to different weed plants associated with various crop plants. Illustrative of prior art herbicide mixtures containing trisubstituted ureas and other compounds are those containing a trichlorophenylacetic acid, its salts, amides or esters (U.S. Pat. No. 3,163,516); alkyl- and/or halo-substituted phenoxy-acetic acid, -salt, -amide or -ester (U.S. Pat. No. 2,709,648); trichlorobenzoic acid or its salts (U.S. Pat. No. 3,253,903); halo- and nitro-substituted diphenyl ethers (U.S. Pat. No. 3,484,230); triazines (U.S. Pat. No. 3,022,150); $CF_3/NO_2$-substituted toluidine (U.S. Pat. No. 3,373,010) and thiolcarbamic acid esters (U.S. Pat. No. 3,095,299).

In further particular, U.S. Pat. No. 2,655,445 discloses a generic class of herbicidal trisubstituted ureas which encompasses chlorotoluron, but this compound is not specifically mentioned. On the other hand, chlorotoluron or analogs or isomers thereof, are specifically-named herbicidal compounds which may be used alone or in conjunction with other named herbicidal compounds, (none of which are acetanilides) in British Pat. Nos. 1,253,143, 1,255,258 and 1,260,460. Herbicidal compositions of chlorotoluron are available, e.g., as Dicurane 80 WP.

It is also known in the prior art to use various 2-halo-2',6'-dialkyl-N-(alkoxyalkyl) acetanilides as herbicides either individually or in combination with other herbicidal componds. For example, U.S. Pat. No. 3,551,132 discloses the herbicidal use of 2-chloro-2',6'-diethyl-N-(methoxymethyl)acetanilide (common name alachlor) admixed with 3'-(carbamoyloxy) anilides. British Pat. No. 1,176,547 discloses the herbicidal use of a mixture of alachlor and linuron, i.e., 3-(3,4-dichlorophenyl)-1-methoxy-1-methylurea.

In still further particular, U.S. Pat. Nos. 3,442,945 and 3,547,620 both of which are also assigned to applicant's assignee, disclose a broad class of herbicidal 2-halo-2',6'-dialkyl-N-(alkoxyalkyl) acetanilides, expressly including N-(butoxymethyl)-6'-tert-butyl-2-chloro-o-acetotoluidide (the nomenclature in said patents follows the acetanilide nomenclature rather than the toluidide nomenclature). This compound has tentatively been designated as "terbuchlor"; application is being made by applicant's assignee to the American Standards Institute for registration of this name as the common name for said compound. Hence, the term "terbuchlor" will sometimes be used hereafter in the specification for brevity. The U.S. Pat. No. 3,442,945 and 3,547,620 both disclose that the acetanilide compounds therein may be admixed with other herbicidal compounds, including certain trisubstituted ureas, such as linuron, monuron or diuron.

Therefore, as pertains to the invention herein, it appears that the closest prior art would be those patents which describe the herbicidal use of the specific components herein, i.e., British Pat. Nos. 1,253,143, 1,255,258 and 1,260,460 for disclosures of herbicides containing chlorotoluron or its isomers or analogs; British Pat. No. 1,176,547 for its disclosure of herbicidal mixtures of alachlor and linuron, and U.S. Pat. Nos. 3,442,945 and 3,547,620 for their disclosures of terbuchlor-containing compositions which may include linuron, monuron or diuron.

Absent from the prior art, to applicant's knowledge, is any recognition or disclosure of a herbicidal composition comprising chlorotoluron and terbuchlor which together impart complementary, supplementary and/or synergistic action with respect, particularly, to undesirable vegetation associated with cereal crops, such as wheat and barley.

The phenomenon of synergism is well knwon to those skilled in the art and, in the herbicidal art, relates to herbicidal compositions of mixed components whose total herbicidal effect is unexpectedly greater than the additive effect of the individual components on particular plants or a spectrum of plants. The use of synergistic mixtures for the control of plant growth permits the utilization of a lesser total amount of herbicidal composition and/or lesser quantities of individual components in the composition to obtain the same or improved results than are obtained when a greater amount of herbicidal composition containing only the individual components or additive mixtures thereof. The use of lesser quantities of active ingredients in a herbicidal composition may also increase the margin of crop safety in the use of those active ingredients.

The concepts of synergism and antagonism (i.e., negative, neutralizing or nullifying effect of one component on another component) in herbicidal combinations have been reduced to mathematical formulation and graphical representation by some authors. For example, by the method described by S. R. Colby in "Weeds", Vol. 15, No. 1 (1967) pages 20–22, the expected response of a combination of herbicides is obtained by taking the product of the percent-of-control values for the individual herbicides and dividing by $(100)^{n-1}$ where $n$ is the number of herbicides in the combination.

Another method of expressing synergism and antagonism is described by P. M. L. Tammes in "Netherlands Journal of Plant Pathology", 70 (1964), 73–80. By the Tammes method, a graphic representation is given of the effect of mixtures of herbicides. Each of the components is expressed as a coordinate on a graph and quantitatively defined effect, e.g., a percent plant mortality, e.g., 50%, 85%, etc., is inserted in the graph. These values are obtained by interpolation. The line which connects the points is called an "isobole". With an isobole the effect of different proportions of the individual components can be evaluated. The Tammes isoboles method has proven reliable in evaluating the synergistic effect of the herbicidal composition of this invention.

As used herein the term "active ingredient" denotes a mixture of terbuchlor and chlorotoluron having the combined supplementary, complementary and synergistic properties unique to this mixture.

The term "plant" as used herein encompasses dormant seeds, germinant seeds, germinative seeds, emerging seedlings and established vegetation including roots and above-ground portions.

The term "control" as used herein is inclusive of the effects of killing, inhibiting the growth, reproduction or proliferation and removing, destroying or otherwise diminishing the occurrence or activity of plants and is applicable to any of the stated effects or combinations thereof.

SUMMARY OF THE INVENTION

The present invention relates to a synergistic herbicidal composition containing as the active ingredient therein a mixture of terbuchlor and chlorotoluron as above defined, and to the herbicidal use of such compositions particularly useful in cereal crops, e.g., wheat and barley, to control undesired plants such as *Lolium multiflorum, Polygonium lapithifolium, Galium aparine, Sinapis arvensis, Stellaria media, Avena fatua, Alopecurus myosuroides* and *Matricaria chamomilla*.

the above-cited U.S. Pat. No. 3,442,945 and 3,547,620, terbuchlor is prepared by reacting 2-tert-butyl-6-methyl-N-methylenaniline and chloroacetyl chloride with n-butanol according to conditions noted in the example.

Chlorotoluron also may be prepared by known methods commonly used to prepare trisubstituted ureas. In general, as exemplified in prior art patents cited above, these ureas are prepared, for example, by reacting the appropriate substituted-phenyl isocyanate, i.e., 3-chloro-4-methylphenyl isocyanate, with the appropriate dialkylamine, e.g., dimethylamine.

Terburchlor and chlorotoluron were tank mixed and applied to the surface of a sandy loam soil contained in plastic pots and previously sown with crop and weed seeds at 1 cm depth. Application of the mixed herbicide was made at a volume equivalent of 4000 l/ha with a Devilbiss atomizer No. 152. Initial irrigation of 1 mm was applied by overhead means and subsequent watering requirements by subirrigation. The plants were visually observed approximately three weeks after sowing and the results recorded.

In the table below, the various plants species tested are identified according to the following abbreviations:

Lol. mul.—*Lolium multiflorum*
Pol. lap.—*Polygonum lapithifolium*
Gal. ap.—*Galium aparine*
Sin,. arv.—*Sinaips arvensis*
Stel. med.—*Stellaria media*
Av. fat.—*Avena fatua*
Alop. myos.—*Alopecurus myosuroides*
Martic. cham.—*Matricaria chamomilla*

TABLE 1

| Active Ingredient | Rate Kg/ha | Wheat | Barley | Lol. Mul. | Pol. lap. | Gal. ap. | Sin. arv. | Stel. med. | Av. fat. | Alop. myos. | Matric. cham. | |
|---|---|---|---|---|---|---|---|---|---|---|---|---|
| | | | | Percent Control of Plants | | | | | | | | |
| Terbuchlor | 4 | 35 | 35 | 60 | 70 | 20 | 50 | 80 | 90 | 90 | 90 | (2) |
| | 2 | 35 | 20 | 100 | 25 | 15 | 50 | 70 | 80 | 85 | 65 | (2) |
| | 1 | 10 | 18 | 100 | 25 | 18 | 40 | 78 | 75 | 85 | 73 | (1) |
| | 0.5 | 5 | 5 | 85 | 13 | 5 | 33 | 43 | 53 | 68 | 70 | (1) |
| | 0.25 | 0 | 0 | 85 | 0 | 0 | 0 | 30 | 40 | 60 | 25 | (2) |
| | 0.125 | 0 | 0 | 50 | 0 | 0 | 0 | 20 | 30 | 20 | 15 | (2) |
| Chlortoluron | 4 | 0 | 5 | 100 | 100 | 60 | 85 | 100 | 100 | 100 | 100 | (2) |
| | 2 | 3 | 5 | 80 | 93 | 48 | 83 | 100 | 48 | 78 | 100 | (1) |
| | 1 | 0 | 5 | 55 | 63 | 8 | 58 | 83 | 13 | 58 | 100 | (1) |
| | 0.5 | 0 | 0 | 13 | 23 | 8 | 43 | 48 | 0 | 13 | 100 | (1) |
| | 0.25 | 0 | 0 | 0 | 15 | 0 | 0 | 30 | 0 | 0 | 100 | (2) |
| Active Ingredient | Rate Kg/ha (3) | Wheat | Barley | Lol. mul. | Pol. lap. | Gal. ap. | sin. arv. | Stel. med. | Av. fat. | Alop. myos. | Matric. cham. | |
| Terbuchlor and Chlortoluron | 2 + 2 | 40 | 100 | 100 | 100 | 100 | 100 | 100 | 100 | 100 | 100 | (2) |
| | 2 + 1 | 30 | 40 | 100 | 80 | 100 | 100 | 100 | 100 | 100 | (2) | |
| | 2 + 0.5 | 10 | 10 | 100 | 85 | 20 | 100 | 100 | 85 | 100 | 100 | (2) |
| | 1 + 2 | 70 | 60 | 100 | 100 | 60 | 100 | 100 | 100 | 100 | 100 | (2) |
| | 1 + 1 | 0 | 5 | 100 | 100 | 80 | 100 | 100 | 100 | 100 | 100 | (2) |
| | 1 + 0.5 | 0 | 10 | 100 | 80 | 20 | 85 | 100 | 80 | 90 | 100 | (2) |
| | 0.5 + 2 | 0 | 75 | 100 | 100 | 85 | 100 | 100 | 100 | 100 | 100 | (2) |
| | 0.5 + 1 | 0 | 25 | 100 | 68 | 38 | 80 | 100 | 78 | 93 | 100 | (1) |
| | 0.5 + 0.5 | 0 | 10 | 100 | 63 | 25 | 63 | 100 | 70 | 88 | 100 | (1) |
| | 0.25 + 1 | 0 | 20 | 100 | 60 | 20 | 60 | 99 | 60 | 85 | 100 | |
| | 0.25 + 0.5 | 0 | 0 | 99 | 50 | 15 | 50 | 80 | 50 | 60 | 100 | (2) |
| | 0.25 + 0.25 | 0 | 0 | 95 | 30 | 20 | 20 | 60 | 40 | 60 | 100 | (2) |
| | 0.125 + 1 | 0 | 25 | 95 | 60 | 0 | 50 | 95 | 40 | 70 | 100 | (2) |
| | 0.125 + 0.5 | 0 | 0 | 95 | 50 | 0 | 15 | 60 | 30 | 30 | 100 | (2) |
| | 0.125 + 0.25 | 0 | 0 | 85 | 40 | 0 | 0 | 30 | 30 | 45 | 100 | (2) |

(1) Percent averages for four replications
(2) Percent averages for two replications
(3) Numbers in the first column refer to terbuchlor rates

DESCRIPTION OF PREFERRED EMBODIMENTS

EXAMPLE

Terbuchlor may be prepared by methods generally known to the art. For example, in Example 4 of each of The synergistic response for terbuchlor/chlorotoluron herbicidal mixtures is well shown by data in Table 1. Thus, consider the average rates of the three herbicides, i.e., terbuchlor, chlorotoluron and a mixture of the two, required to control 85% of the weeds ($GR_{85}$), and the average maximum rates of the herbicides for 15% or less growth reduction ($GR_{15}$) of the crop plants for illustrative purposes.

For example, in order to control *Sinapis arvensis* ($GR_{85}$), an undetermined amount greater than 4 kg/ha of terbuchlor alone is required; however, such rates are not selective for use with wheat and barley. Similarly, 4 kg/ha of chlorotoluron are required for a $GR_{85}$, but here without significant injury to the crop plants. In contrast, terbuchlor/chlorotoluron mixtures of either 1.0 + <1.0 + 0.5 kg/ha will selectively control *Sin. arv.* in wheat and barley. Also, an 0.5 + −2.0 kg/ha mixture will selectively control *Sin. arv.* in barley. The 1.0 + <1.0 kg/ha mixture also controls *Lol. mul*, *Stel. med.*, *Alop. myos.* and *Matri. cham.*, while providing near-adequate control for *Pol. lap* and *Av. fat.*, and the 1.0 + 0.5 kg/ha also controls *Lol. mul.*, *Stel. med.* and *Alop. myos.*

Further, whereas it requires more than 1.0 kg/ha of chlorotoluron and more than 4.0 kg/ha of terbuchlor individually to control *Stel. med.*, (with no selectivity to either wheat or barley as regards terbuchlor), this weed is selectively controlled in wheat and barley by a 0.5 + <0.5 kg/ha terbuchlor/-chlorotoluron combination, and is selectively controlled in wheat by 0.125 + <1.0, 0.25 + <1.0 and 0.5 + <1.0 kg/ha combinations.

Further synergism of the combination herbicide of this invention is shown with respect to *Gal. ap.*, which, when treated with each chemical individually, requires substantially more than 4.0 kg/ha of terbuchlor or chlorotoluron for control, with no safety whatever in wheat or barley (at least, as regards terbuchlor; data for selectivity of chlorotoluron at $GR_{85}$ is not available). However, *Gal. ap.* is selectively controlled with a 0.5 + 2.0 kg/ha terbuchlor/chlorotoluron mixture and is safe for use in wheat fields.

Similarly, from about 3.0–4.0 kg/ha of terbuchlor or chlorotoluron are required to control *Av. fat.* when separately applied (with no safety as regards terbuchlor). However, this weed is effectively controlled with safety in wheat and barley with 1.0 + <1.0 and 2.0 + 0.5 kg/ha terbuchlor/chlorotoluron mixtures, ir a 0.5 + 2.0 kg/ha mixture safe for use in wheat.

Reference to the data in Table 1 further illustrates the synergistic effect of terbuchlor/chlortoluron mixtures to selectively control *Alop. myos.* in wheat and/or barley. It will be noted that when using terbuchlor alone, it requires 1.0 kg/ha to obtain $GR_{85}$ with no selectively towards barley. And, whereas chlorotoluron alone is selective with respect to wheat and barley, it requires greater than 2.0 kg/ha (i.e., 2.86 kg/ha by interpolation) to achieve $GR_{85}$. In contrast, using less than one-half total active ingredient than required for chlorotoluron alone, a 0.5 + 0.5 kg/ha terbuchlor/chlortoluron mixture controls 88% of the *Alop. myos.* weeds, and is selective with respect to both wheat and barley as is a 1.0 + <0.5 kg/ha combination. In addition, other combinations of terbuchlor/chlorotoluron ratios control *Alop. myos.* with selectively toward wheat, e.g., 0.5 + <2.0 kg/ha, 0.5 + <1.0 kg/ha and 0.25 + 1.0 kg/ha.

A Tammes isobole graphic representation of the synergistic effect of terbuchlor/chlorotoluron combinations would show on a coordinate graph the concentration in kg/ha required to achieve $GR_{85}$, for example, with chlorotoluron rates shown along the ordinate (horizontal axis) and terbuchlor rates shown along the abscissa (vertical axis). A line is then drawn to join the $GR_{85}$ rates for each compound; this line is the additive isobole for the mixture. Then holding one of the component rates constant while varying the rate of the other component, data points for each $GR_{85}$ are fixed on the graph. Any combination of weight ratios falling inside (or under) the additive isobole and having a $GR_{85}$ rate for weeds should exhibit synergism, and the corresponding interpolated curve is termed the synergistic isobole. Combinations whose $GR_{85}$ data points fall outside (or above) the additive isobole should exhibit antagonism and the corresponding interpolated curve is termed the antagonistic isobole. Data points falling on the additive isobole line itself represent mixtures whose combined components have only additive effects. If a particular herbicidal combination has a $GR_{85}$ rate for weeds within the area under the additive isobole for that combination, but the data also exhibits injury to the crop greater than 15% at that rate, obviously, the herbicidal combination may not be selective for use in that particular crop under the specific test conditions.

In a specific application of the Tammes isoboles method, data derived from Table 1 is tabulated in Table 2 showing the application rates (in kg/ha) for the individual components terbuchlor and chlorotoluron and various concentration ratios of each in mixtures thereof required to achieve $GR_{85}$ for the specific weed *Sinapis arvensis*. Data points for the $GR_{85}$ rates are fixed on the graph below Table 2 and a line of best fit is drawn through the data points to derive a curve termed the "interpolative synergistic isobole". In the graph, the *x* data points represent $GR_{85}$ data points derived from holding terbuchlor concentrations constant while varying chlorotoluron concentrations and the *o* points represent $GR_{85}$ data points derived from holding chlorotoluron concentrations constant while varying terbuchlor concentrations.

Table 2

Sinapis arvensis $GR_{85}$ rates (kg/ha)

| Terbuchlor |
|---|
| >4.0 |

| Chlortoluron |
|---|
| 4.0 |

| Terbuchlor | + | Chlortoluron |
|---|---|---|
| 0.125 | . | >1.0 |
| 0.250 |   | >1.0 |
| 0.50 |   | 1.3 |
| 1.0 |   | 0.5 |
| 2.0 |   | <0.5 |
| Chlortoluron | + | Terbuchlor |
| 0.25 |   | >0.5 |
| 0.50 |   | 1.0 |
| 1.0 |   | 0.6 |
| 2.0 |   | <0.5 |

Table 2-continued

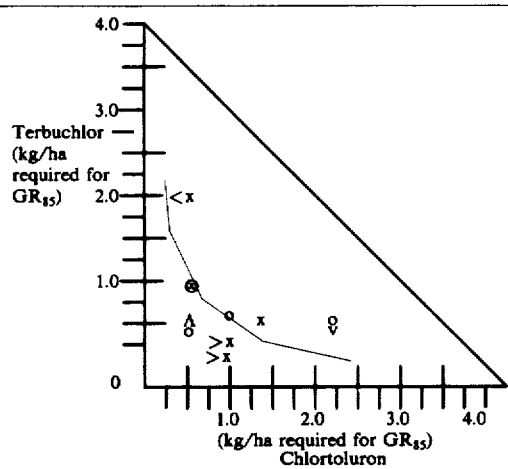

The active ingredient herein can be admixed with one or more adjuvants which can be solid or liquid extenders, carriers, diluents, conditioning agents and the like to form herbicidal compositions. Herbicidal compositions containing the active ingredients of this invention can be formulated with or in the form of granules, wettable powders, aqueous suspensions, dust formulations, emulsifiable oils and solutions in solvents. In general, these formulations can all contain one or more surface-active agents.

Surface-active agents which can be used in herbicidal formulations are well known to those skilled in the art and have been well documented in patents, bulletins and textbooks.

The preparation, formulations and particle size of the granules, wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable powder and dust formulations and from about 5 to 95 parts by weight per 100 parts by weight emulsifiable oil formulations. Formulations containing more or less than the above quantities of active ingredient can easily be prepared by those skilled in the art.

The quantity of active ingredient to be used in the field may vary within certain limits depending upon variables known to those in the art, e.g., condition of the soil, climate, plant, etc. In general, however, amounts ranging from about 0.05 to 6.0 or more kg/ha should be adequate; a preferred range being from about 0.125 to 4.0 kg/ha or suitably, an amount within the range of from 0.250 to 2.0 kg/ha. Terbuchlor/chlorotoluron ratios may vary within fairly wide limits, e.g., from 1:8 to 8:1, a preferred ratio being within the range of from 1:4 to 4:1 or even 1:2 to 2:1.

Application of the herbicidal compositions of this invention to the plant is well-known to those skilled in the art. The application of liquid and particulate solid herbicidal formulations to the above-ground portions of plants can be carried out by conventional methods, e.g., power dusters, boom and hand sprayers and spray dusters. Although in more practical and recommended usage, the herbicidal compositions herein should be applied simultaneously as conjugate components in a mixture. However, it is within the purview of this invention to apply the individual components sequentially in either order, the time interval between successive applications being such as to accomplish the object of this invention, i.e., the supplementary/complementary/synergistic effects of terbuchlor/chlorotoluron combination.

While the illustrative embodiments of the invention have been described herein before with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

I claim:

1. A herbicidal composition consisting essentially of herbicidally effective amount of a mixture of (a) N-(butoxymethyl)-6'-tert-butyl-2-chloro-o-acetotoluidide and (b) N-(3-chloro-4-methyl phenyl)-N',N'-dimethylurea in a weight ratio of (a) to (b) within the range of 1:8 to 8:1 and an inert carrier therefor.

2. Composition according to claim 1 wherein components (a) and (b) together comprise from about 0.5% to 95% by weight of said composition, the balance comprising adjuvant.

3. Composition according to claim 2 wherein the ratio of (a) to (b) is within the range of from about 1:4 to 4:1.

4. A method of controlling undesirable plants associated with cereal crops which comprises applying to the locus of said plants a herbicidally effective amount of a mixture of a. N-(butoxymethyl)-6'-tert-butyl-2-chloro-o-acetotoluidide and
   b. N-(3-chloro-4-methyl phenyl)-N',N'-dimethylurea in a wight ratio within the range of 1:8 to 8:1.

5. Method according to claim 4 wherein components (a) and (b) together comprise from about 0.5% to 95% by weight of said composition, the balance comprising adjuvant.

6. Method according to claim 5 wherein the ratio of (a) to (b) is within the range of from about 1:4 to 4:1.

7. Method according to claim 5 wherein said composition is applied at a rate within the range of from about 0.125 to 4.0 kg/ha.

8. Method according to claim 4 wherein said crops are wheat and barley.

* * * * *